(12) United States Patent
Jones

(10) Patent No.: US 9,936,892 B1
(45) Date of Patent: Apr. 10, 2018

(54) SYSTEMS AND METHODS FOR PROVIDING A FIDUCIAL MARKER

(75) Inventor: Andrew Douglas Jones, Lake Stevens, WA (US)

(73) Assignee: CORTEX MANUFACTURING INC., Lake Stevens, WA (US)

( * ) Notice: Subject to any disclaimer, the term of this patent is extended or adjusted under 35 U.S.C. 154(b) by 317 days.

(21) Appl. No.: 12/764,405

(22) Filed: Apr. 21, 2010

Related U.S. Application Data

(60) Provisional application No. 61/272,243, filed on Sep. 3, 2009, provisional application No. 61/215,263, filed on May 4, 2009.

(51) Int. Cl.
*A61B 5/05* (2006.01)

(52) U.S. Cl.
CPC ..................... *A61B 5/05* (2013.01)

(58) Field of Classification Search
CPC ... A61B 19/54; A61B 2019/5466; A61B 5/05; A61N 2005/1051; A61N 2005/1056
USPC ................................. 600/407–480
See application file for complete search history.

(56) References Cited

U.S. PATENT DOCUMENTS

| | | | |
|---|---|---|---|
| 3,585,553 A | 6/1971 | Muckelroy et al. | |
| 3,706,908 A | 12/1972 | Petri | |
| 4,577,637 A | 3/1986 | Mueller, Jr. | |
| 5,174,302 A * | 12/1992 | Palmer | 600/585 |
| 5,409,004 A | 4/1995 | Sloan | |
| 5,685,306 A * | 11/1997 | Davidson | 600/435 |
| D407,818 S | 4/1999 | Mariant et al. | |
| 5,902,310 A | 5/1999 | Foerster | |
| 6,030,333 A | 2/2000 | Sioshansi | |
| 6,139,488 A * | 10/2000 | Ball | A61F 2/18 600/25 |
| D442,547 S | 5/2001 | Takebuchi et al. | |
| 6,333,971 B2 | 12/2001 | McCrory | |
| 6,382,815 B1 | 5/2002 | Klearman et al. | |
| 6,398,737 B2 * | 6/2002 | Moore et al. | 600/466 |
| 6,419,621 B1 | 7/2002 | Sioshansi | |
| 6,471,630 B1 | 10/2002 | Sioshansi | |
| 6,613,002 B1 * | 9/2003 | Clark | A61B 5/1076 600/104 |
| 6,626,936 B2 * | 9/2003 | Stinson | 623/1.15 |
| 6,687,533 B1 | 2/2004 | Hirano et al. | |
| 7,033,325 B1 * | 4/2006 | Sullivan | 600/585 |
| 7,047,063 B2 | 5/2006 | Burbank | |
| D528,211 S | 9/2006 | Solar et al. | |
| 7,280,865 B2 | 10/2007 | Adler | |
| 7,285,116 B2 * | 10/2007 | de la Rama et al. | 606/27 |
| 7,424,320 B2 | 9/2008 | Chesbrough | |
| 7,565,191 B2 * | 7/2009 | Burbank et al. | 600/431 |
| 8,027,712 B2 | 9/2011 | Sioshansi et al. | |

(Continued)

OTHER PUBLICATIONS

Core Oncology, VISICOIL, Feb. 2008.

(Continued)

*Primary Examiner* — Jennifer Dieterle
*Assistant Examiner* — Vani Gupta
(74) *Attorney, Agent, or Firm* — Seed IP Law Group LLP

(57) ABSTRACT

This invention relates generally to medical devices, and more specifically, to systems and methods for providing a fiducial marker. In one embodiment, a device includes, but is not limited to, one or more markers; and one or more connectors configured to link the one or more markers, wherein at least a portion of the device is detectable via medical imaging.

17 Claims, 10 Drawing Sheets

(56) References Cited

U.S. PATENT DOCUMENTS

| | | | |
|---|---|---|---|
| 8,320,995 | B2 | 11/2012 | Schwamb, Jr. |
| D715,439 | S | 10/2014 | Huang |
| D716,451 | S | 10/2014 | Allen et al. |
| D727,497 | S | 4/2015 | Yang et al. |
| D777,916 | S | 1/2017 | Kuroda et al. |
| 2001/0001809 | A1* | 5/2001 | Berg et al. ............... 600/585 |
| 2002/0022825 | A1* | 2/2002 | Saitou et al. ............. 604/525 |
| 2002/0095205 | A1* | 7/2002 | Edwin ............... A61F 2/07 623/1.13 |
| 2003/0199759 | A1* | 10/2003 | Richard ............... 600/426 |
| 2004/0078071 | A1* | 4/2004 | Escamilla ....... A61B 17/12022 623/1.11 |
| 2005/0065515 | A1 | 3/2005 | Jahng |
| 2005/0154293 | A1* | 7/2005 | Gisselberg ............ A61B 5/06 600/420 |
| 2005/0273002 | A1* | 12/2005 | Goosen et al. ............. 600/414 |
| 2006/0074480 | A1* | 4/2006 | Bales et al. ............. 623/1.15 |
| 2006/0173296 | A1* | 8/2006 | Miller et al. ............. 600/431 |
| 2007/0016233 | A1* | 1/2007 | Ferrera ......... A61B 17/12022 606/159 |
| 2007/0083132 | A1 | 4/2007 | Sharrow |
| 2007/0087026 | A1* | 4/2007 | Field ................. 424/423 |
| 2007/0238983 | A1 | 10/2007 | Suthanthiran |
| 2008/0033286 | A1 | 2/2008 | Whitmore |
| 2008/0234572 | A1 | 9/2008 | Jones |
| 2008/0269601 | A1* | 10/2008 | Schwamb .................. 600/426 |
| 2009/0018403 | A1* | 1/2009 | Black et al. .................. 600/300 |
| 2009/0105584 | A1 | 4/2009 | Jones |
| 2009/0124894 | A1* | 5/2009 | Lamoureux ......... A61N 5/1027 600/426 |
| 2009/0216115 | A1* | 8/2009 | Seiler et al. ............. 600/426 |
| 2011/0028831 | A1 | 2/2011 | Kent |
| 2016/0354178 | A1 | 12/2016 | Mayes et al. |

OTHER PUBLICATIONS

Best Medical International, Best Gold Markers, Jan. 2008.

Dawson et al., "The Reproducibility of Organ Position Using Active Breathing Control (ABC) During Liver Radiotherapy", International Journal of Radiation Oncology Biology Physics, vol. 51, Issue 5, Dec. 1, 2001, pp. 1410-1421.

\* cited by examiner

SYSTEMS AND METHODS FOR PROVIDING A FIDUCIAL MARKER

PRIORITY CLAIM

This application claims the benefit of U.S. provisional patent application Ser. No. 61/215,263 filed May 4, 2009 and U.S. provisional patent application Ser. No. 61/272,243 filed Sep. 3, 2009. The foregoing applications are incorporated by reference in their entirety as if fully set forth herein.

FIELD OF THE INVENTION

This invention relates generally to medical devices, and more specifically, to systems and methods for providing a fiducial marker.

SUMMARY

This invention relates generally to medical devices, and more specifically, to systems and methods for providing a fiducial marker. In one embodiment, a device includes, but is not limited to, one or more markers; and one or more connectors configured to link the one or more markers, wherein at least a portion of the device is detectable via medical imaging.

BRIEF DESCRIPTION OF THE DRAWINGS

Embodiments of the present invention are described in detail below with reference to the following drawings.

DETAILED DESCRIPTION

APPENDIX A is a perspective view of a delivery system for a fiducial marker, in accordance with an embodiment of the invention.

This invention relates generally to medical devices, and more specifically, to systems and methods for providing a fiducial marker. Specific details of certain embodiments of the invention are set forth in the following description and in FIGS. 1-10 and APPENDIX A to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1:
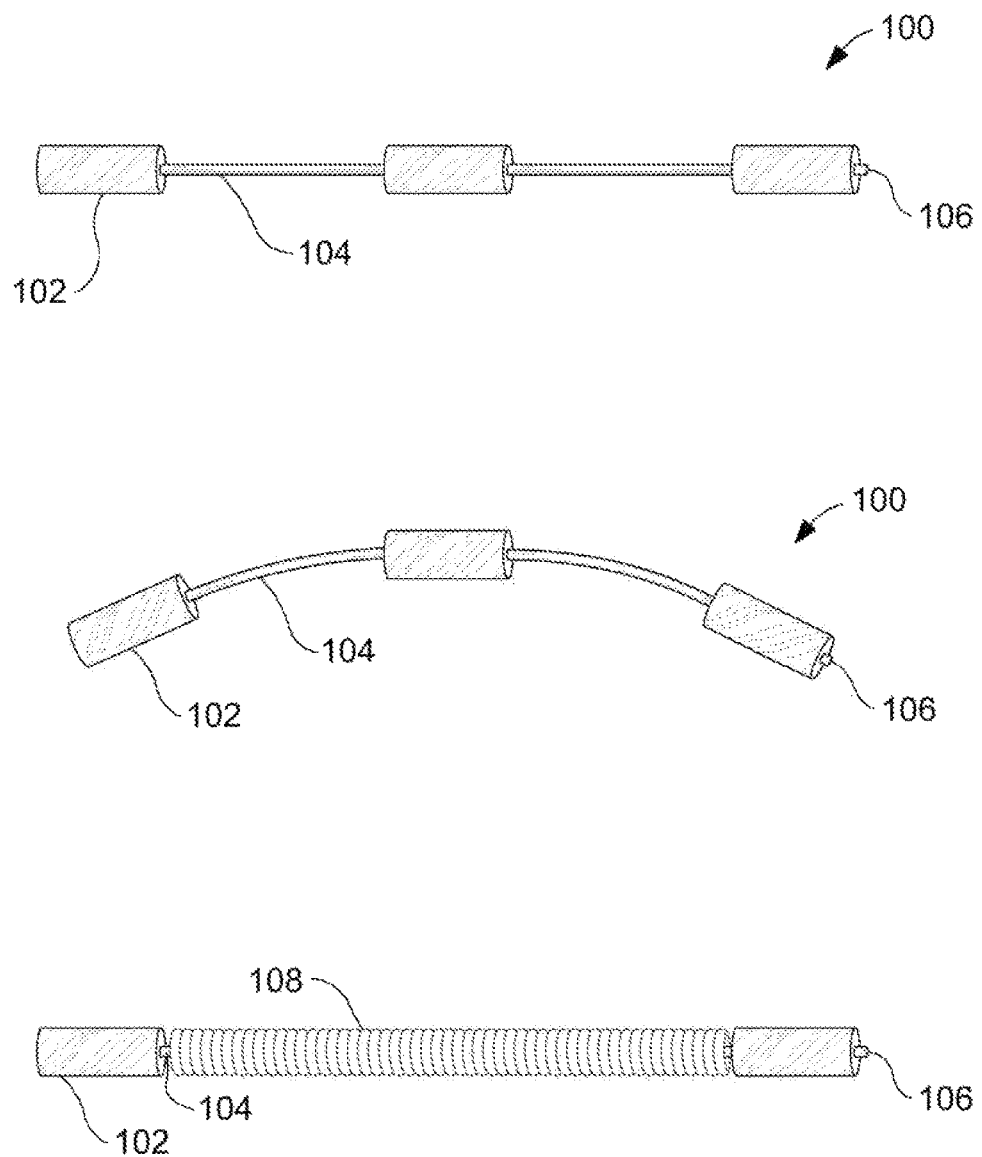
FIG. 1 includes perspective views of a fiducial marker, in accordance with an embodiment of the invention.

FIG. 1 includes perspective views of a fiducial marker, in accordance with an embodiment of the invention. In one embodiment, fiducial marker 100 includes one or more markers 102 and one or more connectors 104 configured to link the one or more markers 102, wherein at least a portion of the fiducial marker 100 is detectable via medical imaging. In one particular embodiment, the one or more connectors 104 are configured as a wire, cord, and/or cable that links the one or more markers 102 by traversing through the one or more markers. In another particular embodiment, the one or more connectors 104 are configured as a wire, cord, and/or cable that links the one or more markers 102 by traversing through the one or more markers 102 and forming one or more flat and/or pointed leads 106. In a further particular embodiment, the one or more markers 102 are approximately 0.5 mm to 1.6 mm in diameter and approximately 1 mm to 10 mm in length. In yet another particular embodiment, the one or more connectors 104 are flexible. Accordingly, in some embodiments, fiducial marker 100 is implantable in vivo within soft tissue for image guided localization and treatment (e.g., RT, IMRT, IGRT, Adaptive RT). Fiducial marker 100 is detectable via medical imaging technologies including, but not limited to, CT, MRI, x-ray, fluoro, ultrasound, portal imaging, mammography, Doppler, PET, SPECT, and/or the like. Treatment guided using fiducial marker 100 may include, but is not limited to, radiation therapy and/or any other medical procedure. In a further particular embodiment, fiducial marker 100 may include at least some radioactive properties. In another embodiment, fiducial marker 100 may be linkable with one or more other fiducial markers (e.g. similar and/or different other fiducial markers). In yet another particular embodiment, fiducial marker 100 may further include a coil 108 portion.

Figure 2:
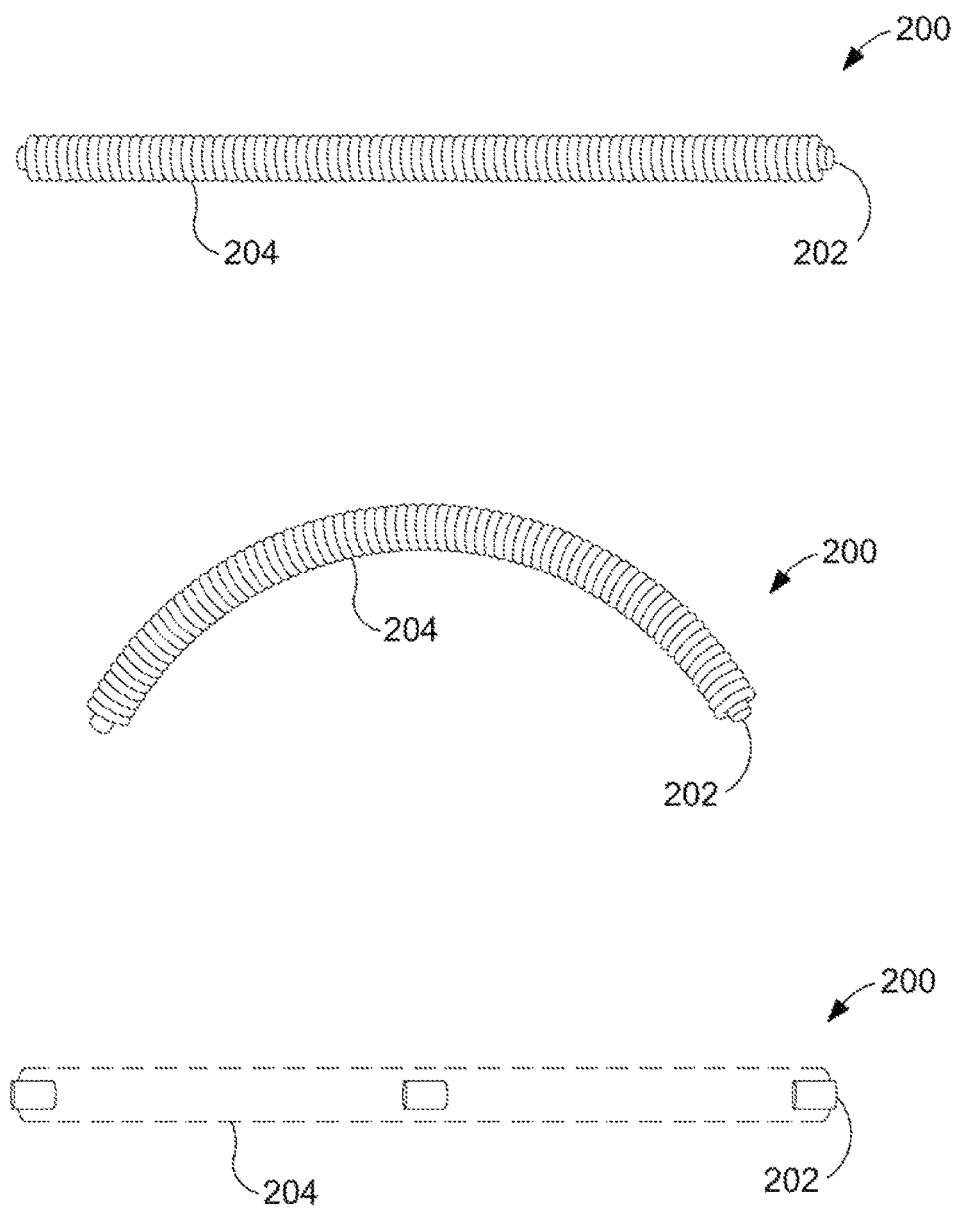
FIG. 2 includes perspective views of a fiducial marker, in accordance with another embodiment of the invention.

FIG. 2 includes perspective views of a fiducial marker, in accordance with another embodiment of the invention. In one embodiment, fiducial marker 200 includes one or more markers 202 and one or more connectors 204 configured to link the one or more markers 202, wherein at least a portion of the fiducial marker 200 is detectable via medical imaging. In one particular embodiment, the one or more connectors 204 are configured as a coil that links the one or more markers 202 by encapsulating the one or more markers 202. In another particular embodiment, the one or more connectors 204 are configured as a coil that links the one or more markers 202 by encapsulating the one or more markers 202 positioned internally at least at opposing ends of the coil. In a further particular embodiment, the one or more connectors 204 are approximately 0.35 mm to 1.6 mm in diameter and at least approximately 1 mm in length. In yet a further particular embodiment, the one or more connectors 204 are flexible. Accordingly, in some embodiments, fiducial marker 200 is implantable in vivo within soft tissue for image guided localization and treatment (e.g., RT, IMRT, IGRT, Adaptive RT). Fiducial marker 200 is detectable via medical imaging technologies including, but not limited to, CT, MRI, x-ray, fluoro, ultrasound, portal imaging, mammography, Doppler, PET, SPECT, and/or the like. Treatment guided using fiducial marker 200 may include, but is not limited to, radiation therapy and/or any other medical procedure. In a further particular embodiment, fiducial marker 200 may include at least some radioactive properties. In another embodiment, fiducial marker 200 may be linkable with one or more other fiducial markers (e.g. similar and/or different other fiducial markers).

Figure 3:
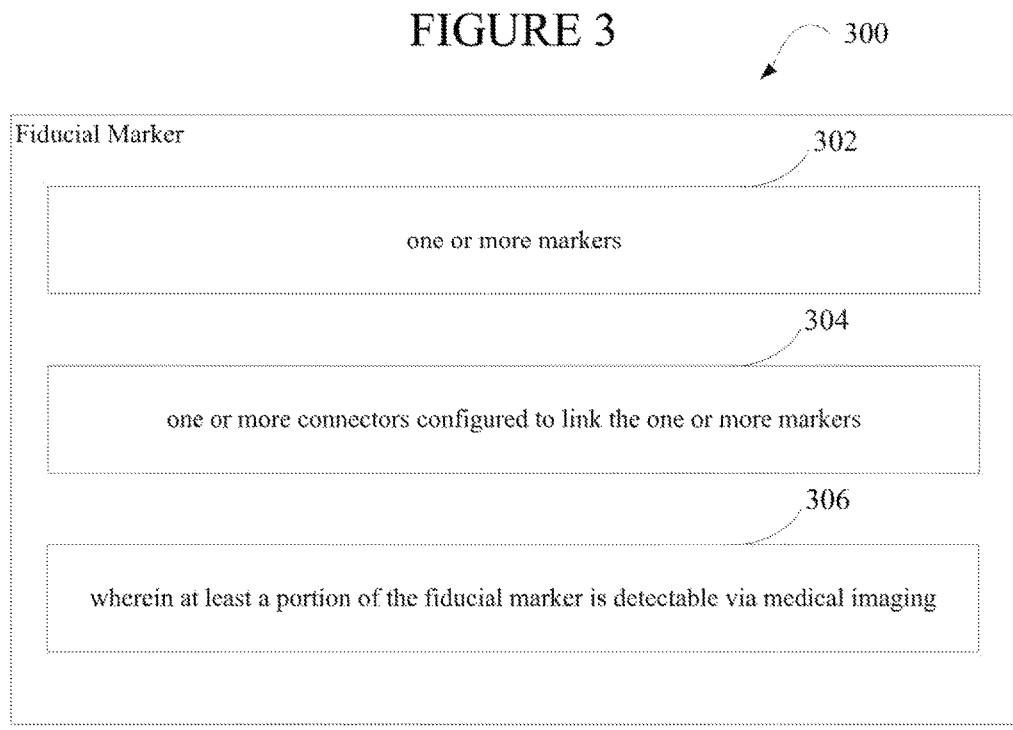
FIG. 3 is a device diagram of a fiducial marker, in accordance with an embodiment of the invention.

FIG. 3 is a device diagram of a fiducial marker, in accordance with an embodiment of the invention. In one embodiment, fiducial marker 300 includes one or more markers 302 and one or more connectors configured to link the one or more markers 304, wherein at least a portion of the fiducial marker is detectable via medical imaging 306. In some embodiments, fiducial marker 300 may be biocompatible and/or configured for single use, wherein fiducial marker 300 may be retained substantially permanently in vivo. In some embodiments, fiducial marker 300 may include one or more additional similar and/or different fiducial markers. In some embodiments, fiducial marker 300 may be a component of a delivery system including a needle and/or cannula (e.g., 22-14 gauge), a stylet, and/or biodegradable wax, wherein fiducial marker 300 is insertable within the needle and/or cannula, retainable using the biodegradable wax (e.g., a biocompatible plug composed of bone wax), and extrudable therefrom using the stylet. In some embodiments, fiducial marker 300 may be storable prior to use in one or more cartridges. In some embodiments, fiducial marker 300 may include one or more customizable components (e.g., customizable connector length, marker type, marker position, or other feature by a physician, technician, and/or assistant at the time of use).

Figure 4:
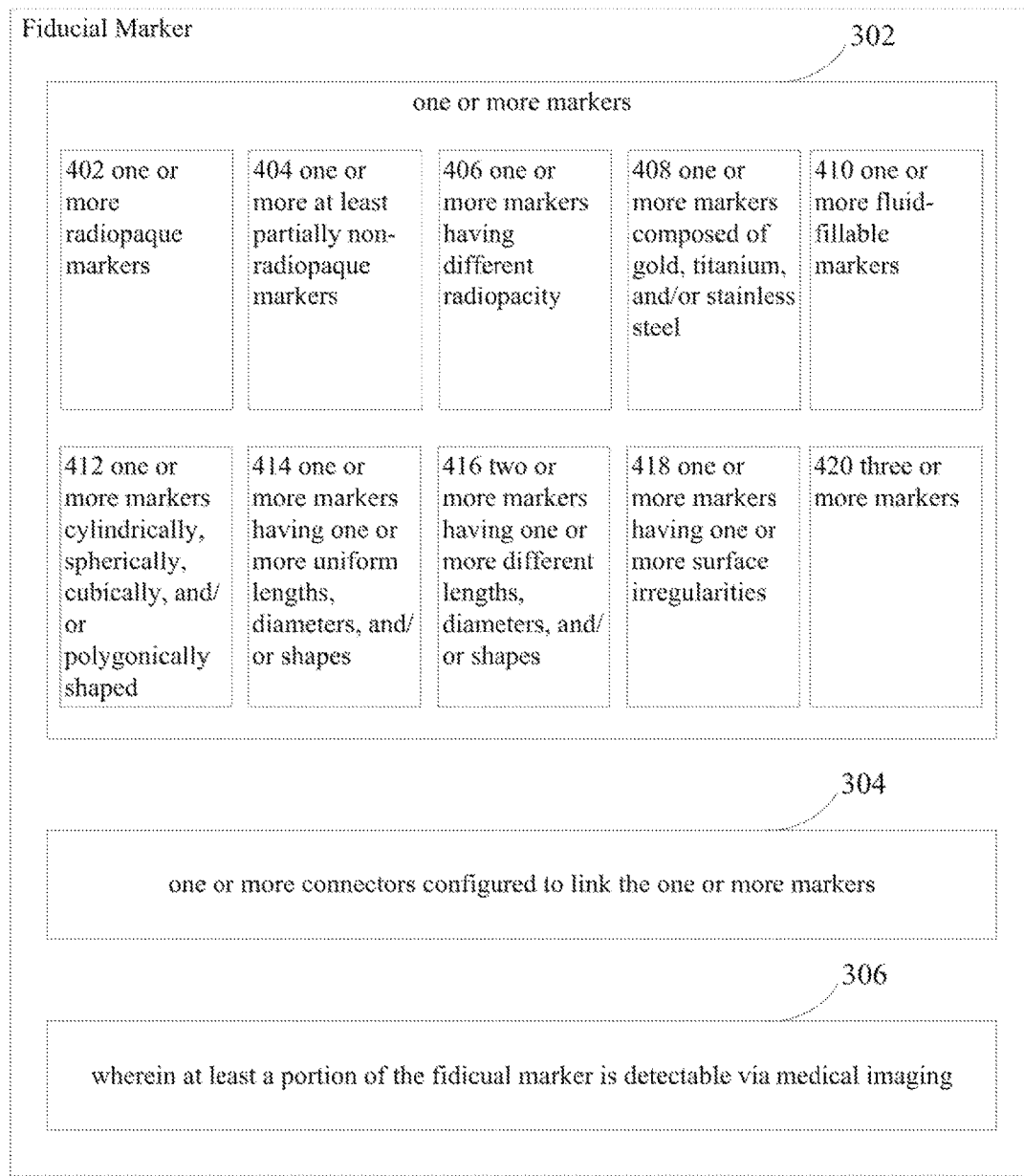
FIGS. 4-6 are device diagrams of a fiducial marker, in accordance with various embodiments of the invention.

FIG. 4 is a device diagram of a fiducial marker, in accordance with various embodiments of the invention. In one embodiment, fiducial marker 300 includes one or more markers 302 and one or more connectors configured to link the one or more markers 304, wherein at least a portion of the fiducial marker is detectable via medical imaging 306. In some embodiments, fiducial marker 300 may include one or more embodiments including, but not limited to, one or more radiopaque markers 402; one or more at least partially non-radiopaque markers 404; one or more markers having different radiopacity 406; one or more markers composed of gold, titanium, and/or stainless steel 408; one or more fluid-fillable markers 410; one or more markers cylindrically, spherically, cubically, and/or polygonically shaped 412; one or more markers having one or more uniform lengths, diameters, and/or shapes 414; two or more markers having one or more different lengths, diameters, and/or shapes 416; one or more markers having one or more surface irregularities 418; and/or three or more markers 420.

In some embodiments, fiducial marker 300 may include one or more radiopaque markers 402. In some embodiments, one or more radiopaque markers 402 are configured to be detectable using CT, MRI, kV/MV x-ray, fluoro, ultrasound, portal imaging, mammography, doppler, PET, SPECT, and/or the like. In some embodiments, one or more radiopaque markers 402 are configured to be detectable using only one type of medical imaging. In some embodiments, one or more radiopaque markers 402 are configured to be detectable using a plurality of types of medical imaging. In some embodiments, fiducial marker 300 includes at least one radiopaque marker 402 configured to be detectable using at least one type of medical imaging and at least one radiopaque marker 402 configured to be detectable using at least one other type of medical imaging.

In some embodiments, fiducial marker 300 may include one or more at least partially non-radiopaque markers 404. In some embodiments, one or more at least partially non-radiopaque markers 404 are configured to be less-detectable or undetectable using medical imaging. In some embodiments, one or more at least partially non-radiopaque markers 404 include a portion that is radiopaque and another portion that is at least partially non-radiopaque. In some embodiments, one or more at least partially non-radiopaque markers 404 are configured to be less-detectable or undetectable for at least one type of medical imaging and more-detectable or detectable for at least one other type of medical imaging. In some embodiments, fiducial marker 300 may include one or more at least partially non-radiopaque markers 404 and one or more radiopaque markers.

In some embodiments, fiducial marker 300 may include one or more markers having different radiopacity 406. In some embodiments, one or more markers having different radiopacity 406 may include a portion that has one radiopacity and at least another portion that has another radiopacity. In some embodiments, one or more markers having different radiopacity 406 may include a portion that has one radiopacity, another portion that has another radiopacity, and at least another portion that has another radiopacity. In some embodiments, one or more markers having different radiopacity 406 may include one or more markers having controllably changeable radiopacity. In some embodiments, one or more markers having different radiopacity 406 may include one or more markers having different radiopacity based upon a type of medical imaging. In some embodiments, one or more markers having different radiopacity 406 may include two or more markers each having different radiopacity. In some embodiments, one or more markers having different radiopacity 406 may include one or more markers having similar radiopacity.

In some embodiments, fiducial marker 300 may include one or more markers composed of gold, titanium, and/or stainless steel 408. In some embodiments, one or more gold markers 408 may include one or more solid-gold markers. In some embodiments, one or more gold markers 408 may include partially-gold markers. In some embodiments, one or more gold markers 408 may be substituted and/or include at least some titanium, stainless steel, and/or other metallic composition. In some embodiments, one or more gold markers 408 may include at least one other marker of a different composition. In some embodiments, one or more gold markers 408 may include at least two other markers of a different composition.

In some embodiments, fiducial marker 300 may include one or more fluid-fillable markers 410. In some embodiments, one or more fluid-fillable markers 410 may include barium, iodine, titanium, tantalum, silver, platinum, iron, iothalamate meglumine, gadopentate dimeglumine-DPTA, silver nitrate, and/or the like that is detectable via medical imaging. In some embodiments, the one or more fluid-fillable markers 410 are fillable and/or emptiable for customizing one or more radiopacity properties. In some embodiments, the one or more fluid-fillable markers 410 include a first portion for one fluid and at least one other portion for another fluid. In some embodiments, the one or more fluid-fillable markers 410 include one or more markers configured to contain different fluid. In some embodiments, the one or more fluid-fillable markers 410 include one or more non-fluid-fillable markers.

In some embodiments, fiducial marker 300 may include one or more markers cylindrically, spherically, cubically, and/or polygonically shaped 412. In some embodiments, one or more markers cylindrically, spherically, cubically, and/or polygonically shaped 412 may include one or more markers that are shaped as a cylinder, sphere, cube, or polygon. In some embodiments, one or more markers cylindrically, spherically, cubically, and/or polygonically shaped 412 may include one or more markers having a combination a cylinder, sphere, cube, and polygon shape. In some embodiments, one or more markers cylindrically, spherically, cubically, and/or polygonically shaped 412 may include and/or be substituted by a different regular and/or irregular shape. In some embodiments, one or more markers cylindrically, spherically, cubically, and/or polygonically shaped 412 may include at least one marker differently shaped.

In some embodiments, fiducial marker 300 may include one or more markers having one or more uniform lengths, diameters, and/or shapes 414. In some embodiments, one or more markers having one or more uniform lengths, diameters, and/or shapes 414 may include a single length, diameter, and/or shape. In some embodiments, one or more markers having one or more uniform lengths, diameters, and/or shapes 414 may include at least one portion having a uniform length, diameter, and/or shape and at least another portion having a different uniform length, diameter, and/or shape. In some embodiments, one or more markers having one or more uniform lengths, diameters, and/or shapes 414 may include at least one portion having a uniform length, diameter, and/or shape and at least another portion having a non-uniform length, diameter, and/or shape. In some embodiments, one or more markers having one or more uniform lengths, diameters, and/or shapes 414 may include at least one marker having one uniform length, diameter, and/or shape and at least one other marker having a different uniform length, diameter, and/or shape. In some embodiments, one or more markers having one or more uniform lengths, diameters, and/or shapes 414 may include one or more markers having a non-uniform length, diameter, and/or shapes.

In some embodiments, fiducial marker 300 may include two or more markers having one or more different lengths, diameters, and/or shapes 416. In some embodiments, two or more markers having one or more different lengths, diameters, and/or shapes 416 may include two or more markers having different uniform lengths, diameters, and/or shapes. In some embodiments, two or more markers having one or more different lengths, diameters, and/or shapes 416 may include two or more markers having different non-uniform lengths, diameters, and/or shapes. In some embodiments, two or more markers having one or more different lengths, diameters, and/or shapes 416 may include at least one marker with a uniform length, diameter, and/or shape and at least one marker with a non-uniform length, diameter, and/or shape. In some embodiments, two or more markers having one or more different lengths, diameters, and/or shapes 416 may include a plurality of markers having a similar length, diameter, and/or shape and at least one marker with a different length, diameter and/or shape.

In some embodiments, fiducial marker 300 may include one or more markers having one or more surface irregularities 418. In some embodiments, one or more markers having one or more surface irregularities 418 may include one or more markers having grooves, patterns, roughness, channels, bumps, dimples, edges, divots, extensions, arms, holes, or the like. In some embodiments, one or more markers having one or more surface irregularities 418 may include one or more markers having at least one portion having one type of surface irregularity and at least another portion having another type of surface irregularity. In some embodiments, one or more markers having one or more surface irregularities 418 may include at least some surface regularity. In some embodiments, one or more markers having one or more surface irregularities 418 may include controllable, adjustable, and/or timed surface irregularities. In some embodiments, one or more markers having one or more surface irregularities 418 may include at least one marker with a surface irregularity and at least another marker with another surface irregularity. In some embodiments, one or more markers having one or more surface irregularities 418 may include at least one marker without surface irregularity.

In some embodiments, fiducial marker 300 may include three or more markers 420. In some embodiments, fiducial marker 300 may include one marker. In some embodiments, fiducial marker 300 may include two markers. In some embodiments, fiducial marker 300 may include three, four, five, six, or more markers (e.g., hundreds or thousands of markers). In some embodiments, three or more markers 420 may be positioned at least substantially at opposing ends of a connector and substantially at a center of a connector. In some embodiments, three or more markers 420 may be positioned just before opposing ends of a connector and substantially at a center of a connector. In some embodiments, three or more markers 420 may be positioned to extend beyond opposing ends of a connector and substantially at a center of a connector. In some embodiments, three or more markers 420 may include three substantially similar markers. In some embodiments, three or more markers 420 may include at least one marker having different properties.

Figure 5:
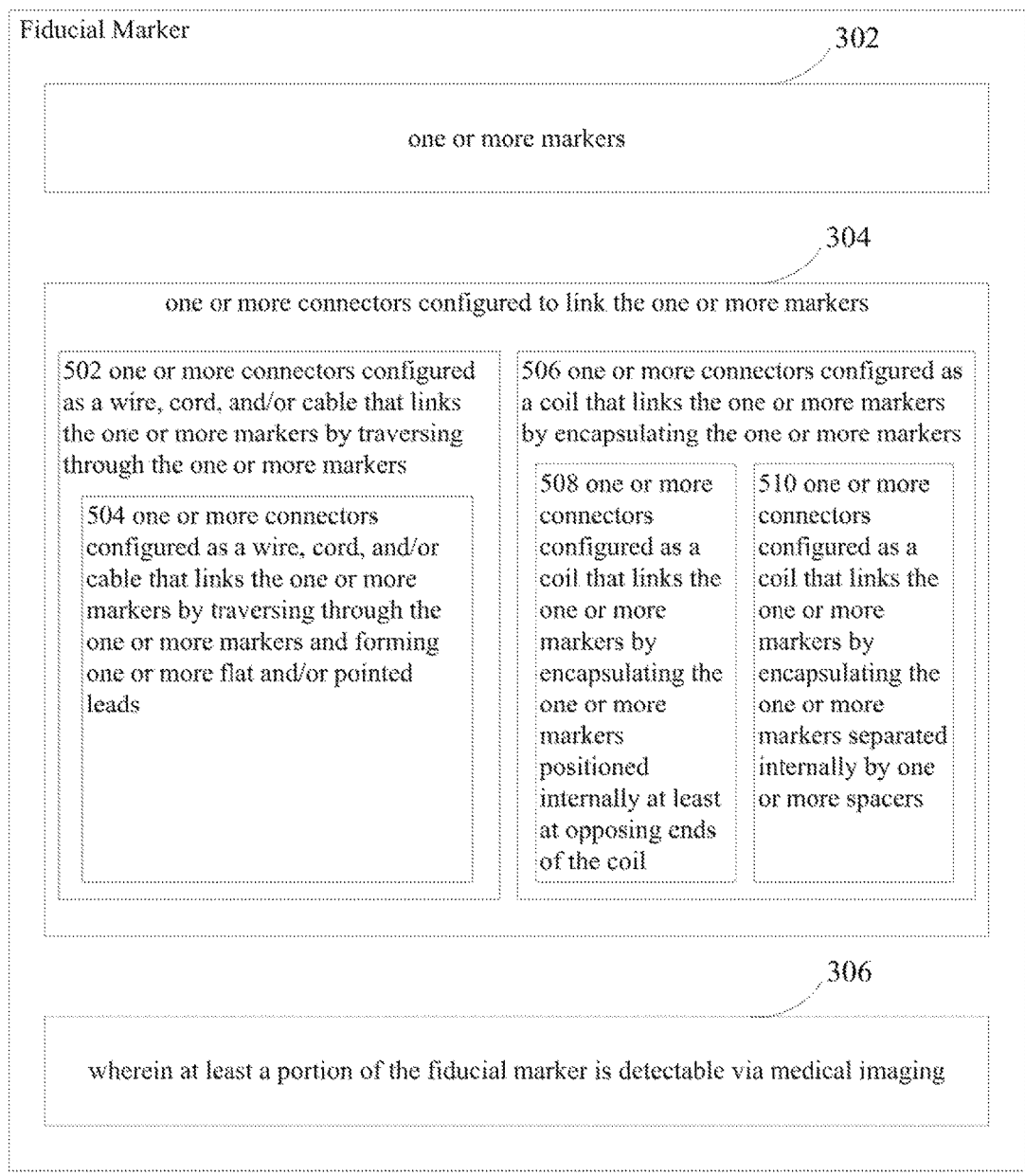

FIG. 5 is a device diagram of a fiducial marker, in accordance with various embodiments of the invention. In one embodiment, fiducial marker 300 includes one or more markers 302 and one or more connectors configured to link the one or more markers 304, wherein at least a portion of the fiducial marker is detectable via medical imaging 306. In some embodiments, fiducial marker 300 may include one or more embodiments including, but not limited to, one or more connectors configured as a wire, cord, and/or cable that links the one or more markers by traversing through the one or more markers 502; one or more connectors configured as a wire, cord, and/or cable that links the one or more markers by traversing through the one or more markers and forming one or more flat and/or pointed leads 504; one or more connectors configured as a coil that links the one or more markers by encapsulating the one or more markers 506; one or more connectors configured as a coil that links the one or more markers by encapsulating the one or more markers positioned internally at least at opposing ends of the coil 508; and/or one or more connectors configured as a coil that links the one or more markers by encapsulating the one or more markers separated internally by one or more spacers 510.

In some embodiments, fiducial marker 300 may include one or more connectors configured as a wire, cord, and/or cable that links the one or more markers by traversing through the one or more markers 502. In some embodiments, one or more connectors configured as a wire, cord, and/or cable that links the one or more markers by traversing through the one or more markers 502 may include one or more connectors having a smaller diameter than the one or more markers. In some embodiments, one or more connectors configured as a wire, cord, and/or cable that links the one or more markers by traversing through the one or more markers 502 may include one or more connectors composed of a single type of wire, cord, and/or cable. In some embodiments, one or more connectors configured as a wire, cord, and/or cable that links the one or more markers by traversing through the one or more markers 502 may include one or more connectors composed of two or more different types of wire, cord, and/or cable. In some embodiments, one or more connectors configured as a wire, cord, and/or cable that links the one or more markers by traversing through the one or more markers 502 may include one connector that links the one or more markers by traversing through the one or more markers. In some embodiments, one or more connectors configured as a wire, cord, and/or cable that links the one or more markers by traversing through the one or more markers 502 may include two or more connectors that link the one or more markers by traversing through the one or more markers. In some embodiments, one or more connectors configured as a wire, cord, and/or cable that links the one or more markers by traversing through the one or more markers 502 may be supplemented with or include one or more connectors that links the one or more markers without traversing through the one or more markers (e.g., over, around, or coupled to a side of a marker).

In some embodiments, fiducial marker 300 may include one or more connectors configured as a wire, cord, and/or cable that links the one or more markers by traversing through the one or more markers and forming one or more flat and/or pointed leads 504. In some embodiments, one or more connectors configured as a wire, cord, and/or cable that links the one or more markers by traversing through the one or more markers and forming one or more flat and/or pointed leads 504 may include one or more connectors that traverse just beyond opposing end markers to form a pointed lead. In some embodiments, one or more connectors configured as a wire, cord, and/or cable that links the one or more markers by traversing through the one or more markers and forming one or more flat and/or pointed leads 504 may include one or more connectors that traverse through without extending beyond opposing end markers to form a flat lead. In some embodiments, one or more connectors configured as a wire, cord, and/or cable that links the one or more markers by traversing through the one or more markers and forming one or more flat and/or pointed leads 504 may include one or more connectors that traverse just beyond one end marker to form a pointed lead and traverse through without extending beyond another end marker.

In some embodiments, fiducial marker 300 may include one or more connectors configured as a coil that links the one or more markers by encapsulating the one or more markers 506. In some embodiments, one or more connectors configured as a coil that links the one or more markers by encapsulating the one or more markers 506 may include a coil that frictionally encapsulates one or more markers. In some embodiments, one or more connectors configured as a coil that links the one or more markers by encapsulating the one or more markers 506 may include a coil that is structurally coupled to and/or joined with one or more markers. In some embodiments, one or more connectors configured as a coil that links the one or more markers by encapsulating the one or more markers 506 may include a coil that frictionally encapsulates at least one marker and that is structurally coupled to and/or joined with at least one other marker. In some embodiments, one or more connectors configured as a coil that links the one or more markers by encapsulating the one or more markers 506 may include a coil that movably links one or more markers. In some embodiments, one or more connectors configured as a coil that links the one or more markers by encapsulating the one or more markers 506 may include a coil that removably links one or more markers.

In some embodiments, fiducial marker 300 may include one or more connectors configured as a coil that links the one or more markers by encapsulating the one or more markers positioned internally at least at opposing ends of the coil 508. In some embodiments, one or more connectors configured as a coil that links the one or more markers by encapsulating the one or more markers positioned internally at least at opposing ends of the coil 508 may include a coil that encapsulates one marker at one end of the coil and another marker at another end of the coil. In some embodiments, one or more connectors configured as a coil that links the one or more markers by encapsulating the one or more markers positioned internally at least at opposing ends of the coil 508 may include a coil that encapsulates one marker at one end of the coil and another marker at another end of the coil with one or both markers extending just beyond an end of the coil. In some embodiments, one or more connectors configured as a coil that links the one or more markers by encapsulating the one or more markers positioned internally at least at opposing ends of the coil 508 may include a coil that encapsulates one marker at one end of the coil and another marker at another end of the coil with an end of the coil extending just beyond one or both markers. In some embodiments, one or more connectors configured as a coil that links the one or more markers by encapsulating the one or more markers positioned internally at least at opposing ends of the coil 508 may include one or more markers positioned at opposing ends of the coil and one or more markers positioned between opposing ends of the coil.

In some embodiments, fiducial marker 300 may include one or more connectors configured as a coil that links the one or more markers by encapsulating the one or more markers separated internally by one or more spacers 510. In some embodiments, one or more connectors configured as a coil that links the one or more markers by encapsulating the one or more markers separated internally by one or more spacers 510 may include one or more spacers composed of a wire, cable, and/or cord. In some embodiments, one or more connectors configured as a coil that links the one or more markers by encapsulating the one or more markers separated internally by one or more spacers 510 may include one or more spacers bio-absorbable and/or biodegradable spacers. In some embodiments, one or more connectors configured as a coil that links the one or more markers by encapsulating the one or more markers separated internally by one or more spacers 510 may include one or more spacers that are expandable and/or movable (e.g. to modify a position of one or more markers such as to designate time). In some embodiments, one or more connectors configured as a coil that links the one or more markers by encapsulating the one or more markers separated internally by one or more spacers 510 may include one or more spacers that separates each of the one or more markers and/or that separates fewer than each of the one or more markers. In some embodiments, one or more connectors configured as a coil that links the one or more markers by encapsulating the one or more markers separated internally by one or more spacers 510 may include one or more spacers that separate one or more markers in an identifiable pattern.

Figure 6:
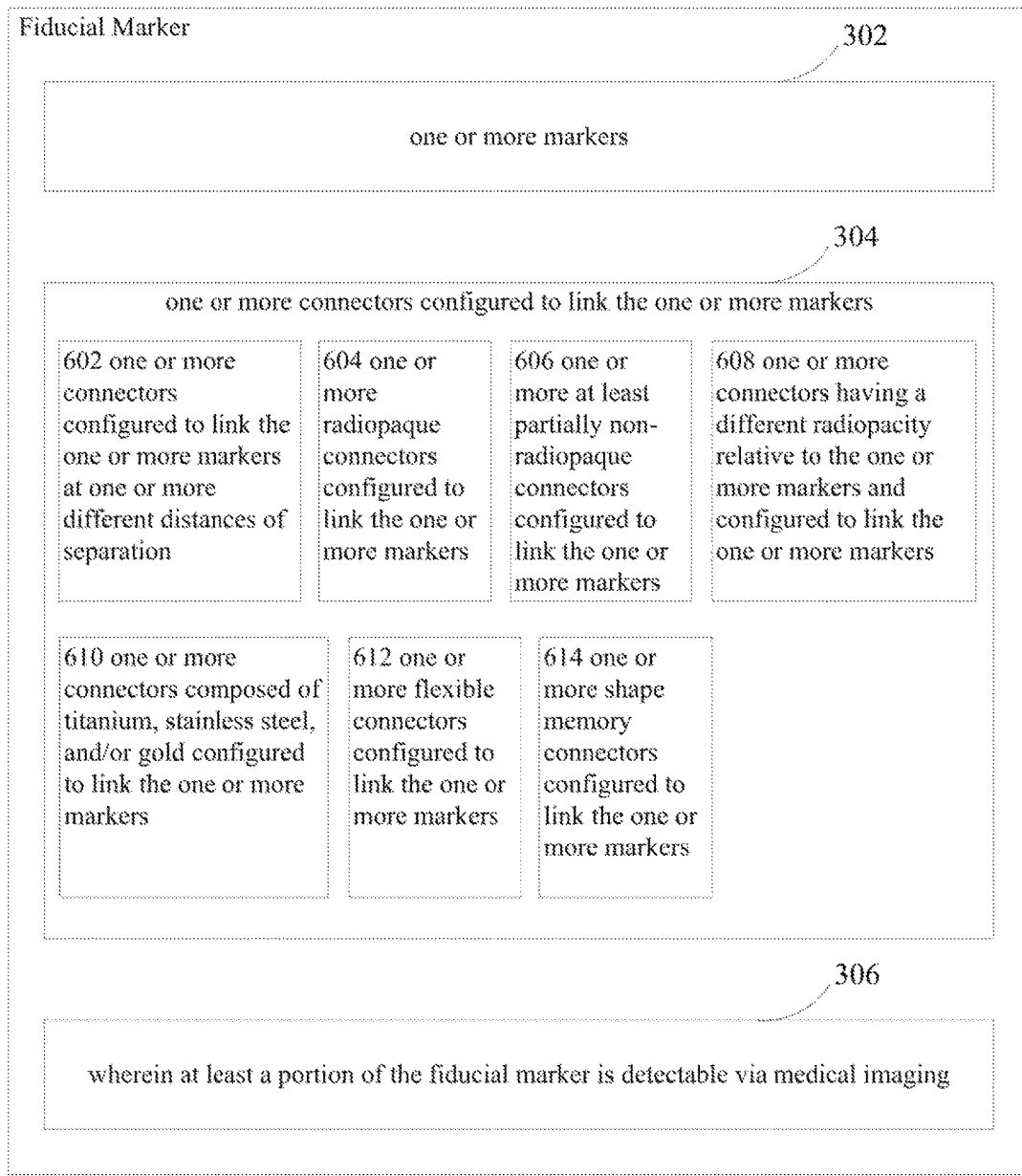

FIG. 6 is a device diagram of a fiducial marker, in accordance with various embodiments of the invention. In one embodiment, fiducial marker 300 includes one or more markers 302 and one or more connectors configured to link the one or more markers 304, wherein at least a portion of the fiducial marker is detectable via medical imaging 306. In some embodiments, fiducial marker 300 may include one or more embodiments including, but not limited to, one or more connectors configured to link the one or more markers at one or more different distances of separation 602; one or more radiopaque connectors configured to link the one or more markers 604; one or more at least partially non-radiopaque connectors configured to link the one or more markers 606; one or more connectors having a different radiopacity relative to the one or more markers and configured to link the one or more markers 608; one or more connectors composed of titanium, stainless steel, and/or gold configured to link the one or more markers 610; one or more flexible connectors configured to link the one or more markers 612; and one or more shape memory connectors configured to link the one or more markers 614.

In some embodiments, fiducial marker 300 may include one or more connectors configured to link the one or more markers at one or more different distances of separation 602. In some embodiments, one or more connectors configured to link the one or more markers at one or more different distances of separation 602 may include one or more connectors configured to link one or more markers equidistantly. In some embodiments, one or more connectors configured to link the one or more markers at one or more different distances of separation 602 may include one or more connectors configured to link at least some markers equidistantly and at least other markers at different distances of separation. In some embodiments, one or more connectors configured to link the one or more markers at one or more different distances of separation 602 may include one or more connectors configured to link the one or more markers at distances of separation that correspond with units of measurement (e.g., enabling the markers to suggest distances). In some embodiments, one or more connectors configured to link the one or more markers at one or more different distances of separation 602 may include one or more connectors configured to link one or more markers at one or more adjustable distances of separation.

In some embodiments, fiducial marker 300 may include one or more radiopaque connectors configured to link the one or more markers 604. In some embodiments, one or more radiopaque connectors configured to link the one or more markers 604 may include one or more uniformly radiopaque connectors. In some embodiments, one or more radiopaque connectors configured to link the one or more markers 604 may include one or more non-uniformly radiopaque connectors (e.g., one portion with one radiopacity and another portion with another radiopacity and/or increased radiopacity towards an end of a connector). In some embodiments, one or more radiopaque connectors configured to link the one or more markers 604 may include one or more radiopaque connectors configured to be detectable for one or more types of medical imaging and less-detectable and/or undetectable for one or more other types of medical imaging.

In some embodiments, fiducial marker 300 may include one or more at least partially non-radiopaque connectors configured to link the one or more markers 606. In some embodiments, one or more at least partially non-radiopaque connectors configured to link the one or more markers 606 may include one or more connectors that are uniformly partially non-radiopaque. In some embodiments, one or more at least partially non-radiopaque connectors configured to link the one or more markers 606 may include one or more connectors that are non-uniformly partially non-radiopaque (e.g., one portion with one non-radiopacity and another portion with another non-radiopacity and/or increased non-radiopacity towards a center of a connector). In some embodiments, one or more at least partially non-radiopaque connectors configured to link the one or more markers 606 may include one or more at least partially non-radiopaque connectors configured to be less-detectable and/or un-detectable for one or more types of medical imaging and more detectable for one or more other types of medical imaging. In some embodiments, one or more at least partially non-radiopaque connectors configured to link the one or more markers 606 may include one or more substantially non-radiopaque connectors.

In some embodiments, fiducial marker 300 may include one or more connectors having a different radiopacity relative to the one or more markers and configured to link the one or more markers 608. In some embodiments, one or more connectors having a different radiopacity relative to the one or more markers and configured to link the one or more markers 608 may include one or more connectors having one radiopacity and one or more markers having a different radiopacity (e.g., markers having increased radiopacity). In some embodiments, one or more connectors having a different radiopacity relative to the one or more markers and configured to link the one or more markers 608 may include one or more connectors having a different radiopacity relative to at least one marker and a similar radiopacity relative to at least another marker. In some embodiments, one or more connectors having a different radiopacity relative to the one or more markers and configured to link the one or more markers 608 may include one or more connectors having a radiopacity configured to be detectable for one or more types of medical imaging and one or more markers having a radiopacity configured to be detectable for one or more other types of medical imaging.

In some embodiments, fiducial marker 300 may include one or more connectors composed of titanium, stainless steel, and/or gold configured to link the one or more markers 610. In some embodiments, one or more connectors composed of titanium, stainless steel, and/or gold configured to link the one or more markers 610 may include only one of the foregoing materials and/or a combination of the foregoing materials. In some embodiments, one or more connectors composed of titanium, stainless steel, and/or gold configured to link the one or more markers 610 may include one portion composed of one material and at least one other portion composed of another material. In some embodiments, one or more connectors composed of titanium, stainless steel, and/or gold configured to link the one or more markers 610 may be substituted and/or complemented with another pure metal, alloy, or other composition either biocompatible and/or bioabsorbable. In some embodiments, one or more connectors composed of titanium, stainless steel, and/or gold configured to link the one or more markers 610 may include one or more connectors composed of a similar and/or different material to one or more markers. In some embodiments, one or more connectors composed of titanium, stainless steel, and/or gold configured to link the one or more markers 610 may be composed of a similar material to at least one marker and a different material to at least one other marker.

In some embodiments, fiducial marker 300 may include one or more flexible connectors configured to link the one or more markers 612. In some embodiments, one or more flexible connectors configured to link the one or more markers 612 may include one or more uniformly flexible connectors. In some embodiments, one or more flexible connectors configured to link the one or more markers 612 may include one or more non-uniformly flexible connectors (e.g. a first rigid portion and a second flexible portion). In some embodiments, one or more flexible connectors configured to link the one or more markers 612 may include one or more connectors configurable to flex with substantially low to no resistance (e.g., to such a degree to prevent damage to soft tissue of a body). In some embodiments, one or more flexible connectors configured to link the one or more markers 612 may include one or more connectors configurable to flex and retain the flexed position without reverting back to the pre-flex position. In some embodiments, one or more flexible connectors configured to link the one or more markers 612 may include one or more flexible connectors configured to flexibly rotate and/or bend. In some embodiments, one or more flexible connectors configured to link the one or more markers 612 may be substituted with and/or complemented with one or more connectors configured to articulate at one or more joints.

In some embodiments, fiducial marker 300 may include one or more shape memory connectors configured to link the one or more markers 614. In some embodiments, one or more shape memory connectors configured to link the one or more markers 614 may include one or more connectors uniformly exhibiting shape memory properties. In some embodiments, one or more shape memory connectors configured to link the one or more markers 614 may include one or more connectors non-uniformly exhibiting shape memory properties (a first portion of a connector having shape memory properties and another portion of a connector without shape memory properties). In some embodiments, one or more shape memory connectors configured to link the one or more markers 614 may include one or more temperature sensitive shape memory components (e.g., a connector configured to assume a particular shape at approximately body temperature). In some embodiments, one or more shape memory connectors configured to link the one or more markers 614 may include one or more connectors that assume a particular shape upon release from a different shape.

Figure 7:
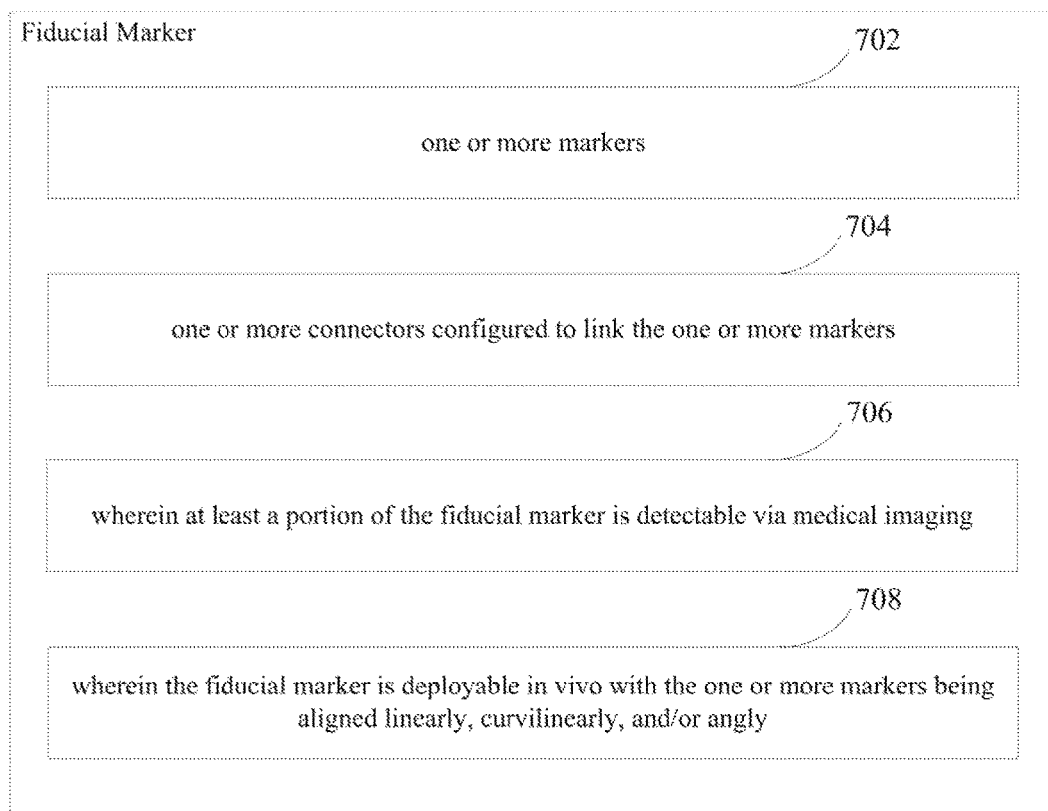
FIG. 7 is a device diagram of a fiducial marker, in accordance with another embodiment of the invention.

FIG. 7 is a device diagram of a fiducial marker, in accordance with another embodiment of the invention. In one embodiment, fiducial marker 700 includes one or more markers 702 and one or more connectors configured to link the one or more markers 704, wherein at least a portion of the fiducial marker is detectable via medical imaging 706, and wherein the fiducial marker is deployable in vivo with the one or more markers being aligned linearly, curvilinearly, and/or angly 708. In some embodiments, fiducial marker 700 may be deployable in soft tissue of a human. In some embodiments, fiducial marker 700 may be deployable in another location and/or in an animal. In some embodiments, fiducial marker 700 may be deployable using a needle and/or cannula with a stylet for extruding fiducial marker from the needle and/or cannula (e.g. needle and/or cannula may be withdrawn while maintaining stylet in a substantially fixed position or needle and/or cannula may be maintained in a substantially fixed position while stylet is advanced). In some embodiments, fiducial marker 700 may be alterable automatically and/or manually substantially during deployment (e.g., fiducial marker 700 may be cut to define a length and/or a quantity of markers). In some embodiments, fiducial marker 700 may be deployable with one or more markers being aligned substantially linearly with one or more connectors. In some embodiments, fiducial marker 700 may be deployable with one or more markers being aligned along a curve with one or more connectors (e.g. convex and/or concave relative to a location). In some embodiments, fiducial marker 700 may be deployable with one or more markers being aligned at an angle along with one or more connectors (e.g., a single angle and/or two or more angles). In some embodiments, fiducial marker 700 may be deployable in a linear, curvilinear, and/or angled form. In some embodiments, fiducial marker 700 may be deployable in one form (e.g., linear) before assuming another form, such as through shape memory and/or through movement of a needle and/or cannula during deployment. In some embodiments, fiducial marker 700 may be deployable using a fixed and/or removable needle and/or cannula attachment that facilitates a desired alignment (e.g. a curved attachment).

Figure 8:
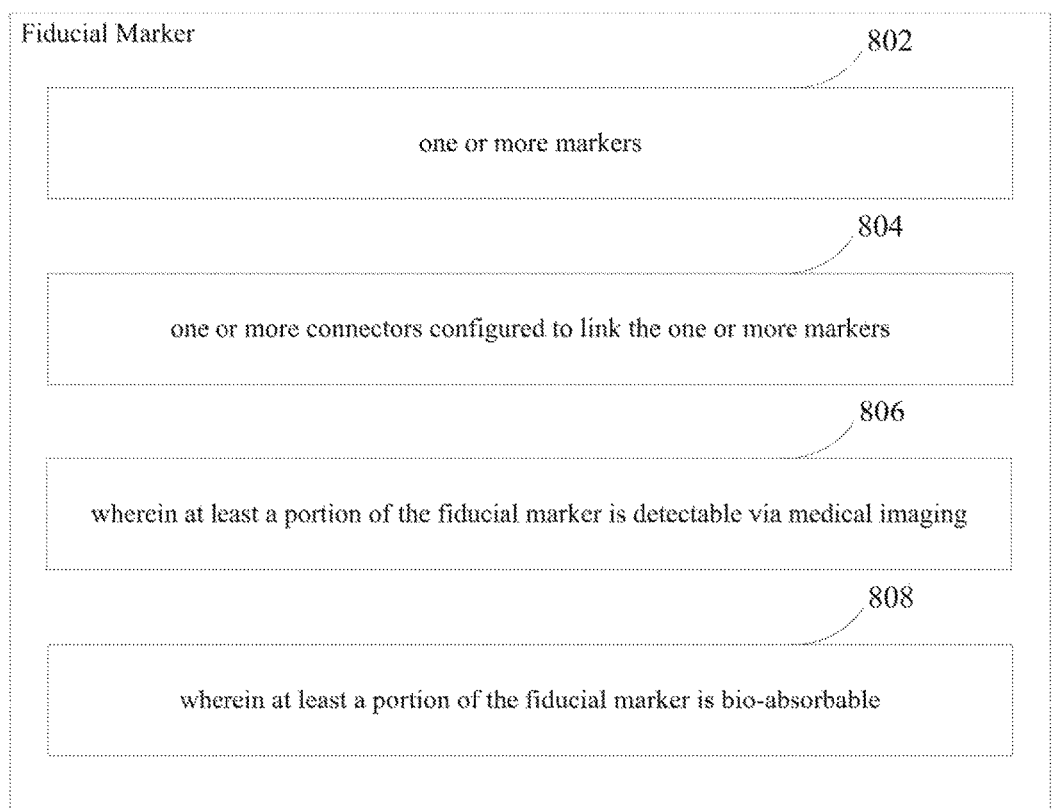
FIG. 8 is a device diagram of a fiducial marker, in accordance with another embodiment of the invention.

FIG. 8 is a device diagram of a fiducial marker, in accordance with another embodiment of the invention. In one embodiment, fiducial marker 800 includes one or more markers 802 and one or more connectors configured to link the one or more markers 804, wherein at least a portion of the fiducial marker is detectable via medical imaging 806, and wherein at least a portion of the fiducial marker is bio-absorbable 808. In some embodiments, at least a portion of the fiducial marker being bio-absorbable 808 may include at least a portion of one or more markers, at least a portion of one or more connectors, and/or at least a portion of another embodiment disclosed herein (e.g., spacer, sheath, needle plug). In some embodiments, at least a portion of the fiducial marker being bio-absorbable 800 may include being biodegradable and/or bioabsorbable.

Figure 9:
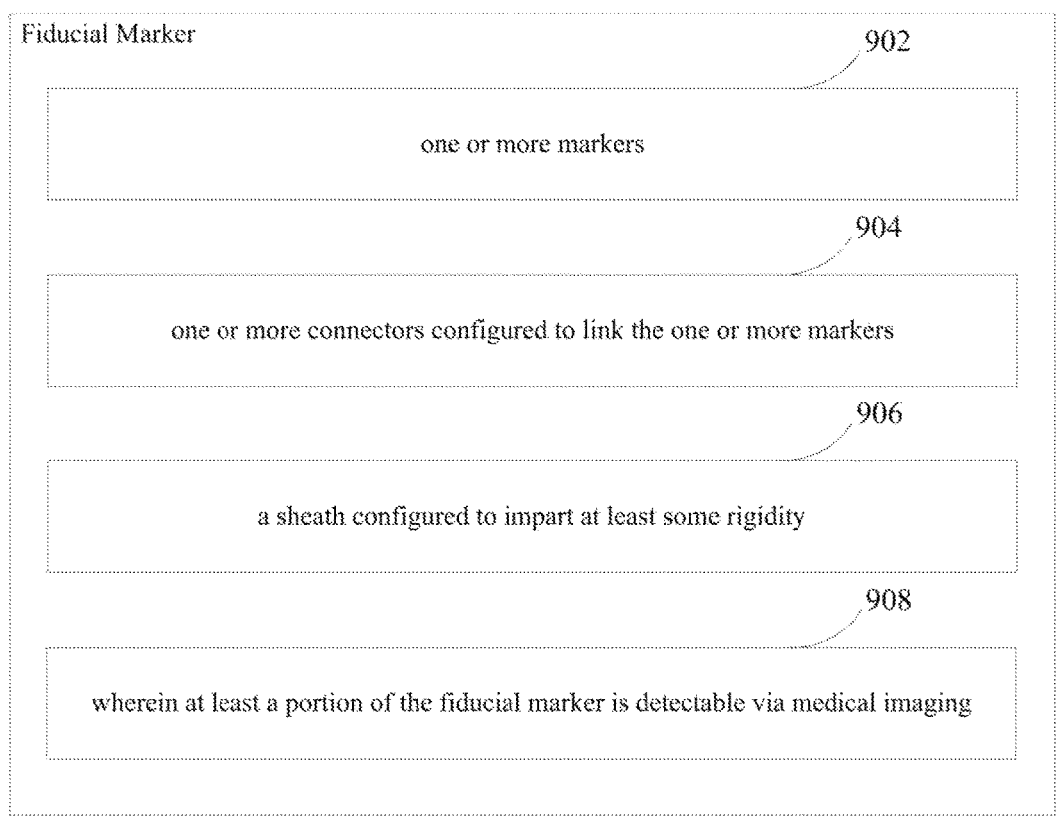
FIG. 9 is a device diagram of a fiducial marker, in accordance with another embodiment of the invention.

FIG. 9 is a device diagram of a fiducial marker, in accordance with another embodiment of the invention. In one embodiment, fiducial marker 900 includes one or more markers 902 and one or more connectors configured to link the one or more markers 904, wherein at least a portion of the fiducial marker is detectable via medical imaging 906, and a sheath configured to impart at least some rigidity 908. In some embodiments, a sheath 908 may be composed of a bioabsorbable and/or biodegradable composition. In some embodiments, a sheath 908 may encapsulate at least a portion of one or more markers and/or one or more connectors. In some embodiments, a sheath 908 may be inserted within at least a portion of one or more connectors. In some embodiments, a sheath 908 may be shrink-wrapped in position to impart at least some rigidity to fiducial marker. In some embodiments, a sheath 908 may impart at least some rigidity in a form of a linear, curvilinear, and/or angled alignment.

Figure 10:
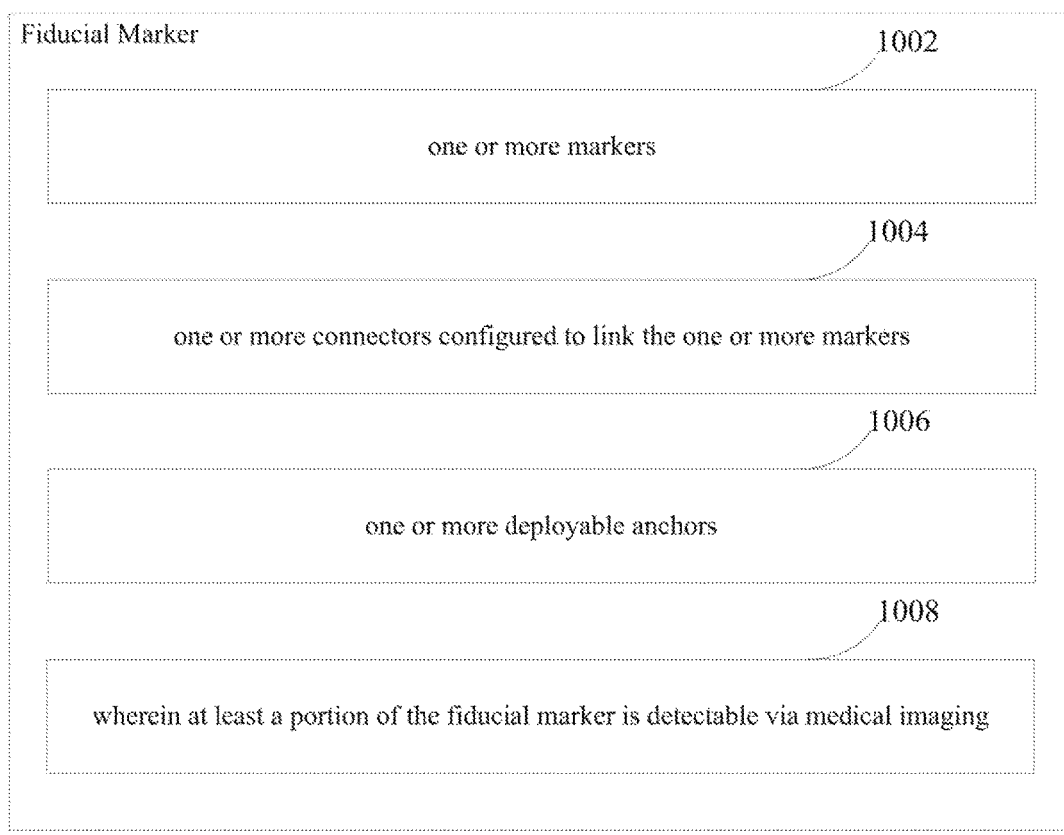
FIG. 10 is a device diagram of a fiducial marker, in accordance with another embodiment of the invention.

FIG. 10 is a device diagram of a fiducial marker, in accordance with another embodiment of the invention. In one embodiment, fiducial marker 1000 includes one or more markers 1002, one or more connectors configured to link the one or more markers 1004, and one or more deployable anchors 1006, wherein at least a portion of the fiducial marker is detectable via medical imaging 1008. In some embodiments, one or more deployable anchors 1006 may include one or more fixed position and/or movable anchors. In some embodiments, one or more deployable anchors 1006 may be surface roughness of one or more markers and/or one or more connectors. In some embodiments, one or more deployable anchors 1006 may include a protrusion and/or extension from one or more markers and/or one or more connectors. In some embodiments, one or more deployable anchors 1006 may be at least partially radiopaque or non-radiopaque. In some embodiments, one or more deployable anchors 1006 may be removable and/or movable relative to one or more markers and/or one or more connectors.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A fiducial marker, comprising:
three or more markers having a first radiopacity; and
one or more connectors having a second radiopacity different from the first radiopacity, the one or more connectors configured as a coil that encapsulates the three or more markers, the three or more markers separate and distinct from the coil, the three or more markers contained and linearly, curvilinearly, or angly affixed within a tubular space formed by the coil, each of the three or more markers spaced equidistant from one other of the three or more markers,
wherein the fiducial marker is arranged for implantation in vivo within soft tissue, and wherein the one or more connectors and the three or more markers of the fiducial marker are detectable via medical imaging.

2. The fiducial marker of claim 1, wherein the one or more connectors configured as a coil at least partially encapsulates a first marker of the three or more markers at one end of the coil and at least partially encapsulates a second marker of the three or more markers at another end of the coil with one or both of the first and second markers extending just beyond their respective end of the coil.

3. The fiducial marker of claim 1, wherein the one or more connectors configured as a coil completely encapsulates one marker at one end of the coil and completely encapsulates another marker at another end of the coil with the one end of the coil extending just beyond the one marker and the other end of the coil extending just beyond the other marker.

4. The fiducial marker of claim 1, wherein the one or more connectors configured as a coil includes tightly wound coils at one end of the coil to frictionally encapsulate a first marker of the three or more markers, tightly wound coils at another end of the coil to frictionally encapsulate a second marker the three or more markers, and less tightly wound coils between the first and second markers to permit the fiducial marker to flex.

5. The fiducial marker of claim 4, wherein at least two of the three or more markers are titanium and the coil is gold.

6. The fiducial marker of claim 4, wherein the less tightly wound coils between the first and second markers encapsulate a third marker.

7. The fiducial marker of claim 1, wherein the three or more markers are fixed permanently at a known distance from each other within an inner cylindrical portion of the coil.

8. The fiducial marker of claim 1, wherein the fiducial marker has a length and diameter sized for deployment in vivo with a needle or with a cannular medical device.

9. A fiducial marker, comprising:
at least one connector configured as a coil, the coil having a first end, a second end opposed to the first end, and a central portion;
a first marker encapsulated within a tubular space formed by the coil and affixed at the first end of the coil;
a second marker encapsulated within the tubular space formed by the coil; and
a third marker encapsulated within the tubular space formed by the coil and affixed at the second end of the coil, wherein the fiducial marker is arranged for implantation in vivo within soft tissue, and wherein the coil and the first, second, and third markers of the fiducial marker are detectable via medical imaging, wherein the fiducial marker is formed from at least two different materials having different radiopacities, the at least two different materials distinguishable from each other in representative images produced via the medical imaging.

10. The fiducial marker of claim 9, wherein the fiducial marker is formed from at least two different materials, a first one of the at least two different materials being a bioabsorbable material and a second one of the at least two different materials including at least one of gold, titanium, and stainless steel.

11. The fiducial marker of claim 9, wherein the coil is structurally coupled to the first marker and structurally coupled to the third marker.

12. The fiducial marker of claim 11, wherein a first area of the coil encapsulating the first marker is rigid, wherein a second area of the coil encapsulating the second marker is flexible, and wherein a third area of the coil encapsulating the third marker is rigid.

13. A medical procedure, comprising:
identifying a soft tissue area in a patient's body where a fiducial marker will be placed in vivo, the fiducial marker having one or more connectors having a first radiopacity configured as a coil and at least three markers having radiopacity different from the first radiopacity encapsulated and structurally coupled within an inner cylindrical portion of the coil, wherein the coil and the at least three markers of the fiducial marker are detectable via medical imaging; and
deploying the fiducial marker in the identified soft tissue area of the patient's body.

14. The medical procedure of claim 13, comprising:
performing an imaging procedure on the identified soft tissue area of the patient; and
identifying a representation of the fiducial marker on an output image produced by the imaging procedure.

15. The medical procedure of claim 13, comprising:
distinguishing in the representation of the fiducial marker the coil of the fiducial marker from a first one of the at least three markers of the fiducial marker, the coil and the first one of the at least three markers of the fiducial marker formed from different materials having different radiopacities.

16. The medical procedure of claim 13, wherein a first portion of the coil is rigid where the coil encapsulates a first one of the at least three markers and a second portion of the coil is flexible.

17. The medical procedure of claim 13, wherein deploying the fiducial marker includes providing the fiducial marker inside a needle or a cannular medical device.

* * * * *